United States Patent
Macrae

(10) Patent No.: US 6,949,088 B2
(45) Date of Patent: Sep. 27, 2005

(54) EAR IRRIGATION DEVICE

(75) Inventor: John Macrae, Carlisle (CA)

(73) Assignee: Earigate Inc., Burlington (CA)

( * ) Notice: Subject to any disclaimer, the term of this patent is extended or adjusted under 35 U.S.C. 154(b) by 17 days.

(21) Appl. No.: 10/162,887

(22) Filed: Jun. 6, 2002

(65) Prior Publication Data

US 2003/0229322 A1 Dec. 11, 2003

(30) Foreign Application Priority Data

Jun. 5, 2002 (CA) .............................. 2389398

(51) Int. Cl.$^7$ ............................ A61M 31/00
(52) U.S. Cl. ..................... 604/275; 604/514
(58) Field of Search ................ 604/28, 43, 514, 604/93.01, 117, 118, 131, 150, 173, 187, 257, 275, 276, 289, 290, 310, 911; 606/162

(56) References Cited

U.S. PATENT DOCUMENTS

| | | | |
|---|---|---|---|
| 1,779,268 A | * 10/1930 | Belfrage et al. | ............... 604/39 |
| 2,576,766 A | 11/1951 | Sokolik | |
| 4,206,756 A | 6/1980 | Grossan | |
| 5,364,343 A | 11/1994 | Apolet et al. | |
| 6,210,358 B1 | 4/2001 | Roger | |

FOREIGN PATENT DOCUMENTS

| | | | |
|---|---|---|---|
| GB | 2 318 736 | | 5/1998 |
| WO | WO 84/02655 | * | 7/1984 |

OTHER PUBLICATIONS

PCT International Search Report (Corrected Version), re PCT/CA03/00836, John Macrae, dated Oct. 1, 2003.

* cited by examiner

*Primary Examiner*—Nicholas D. Lucchesi

(57) ABSTRACT

The invention provides an ear irrigation device for injecting a fluid into an external ear canal extending between an external ear and a tympanic membrane. The external ear canal includes an outer portion extending inwardly from the external ear and including cerumen-producing glands and an inner portion between the tympanic membrane and the outer portion. The ear irrigation device has a longitudinally extending body including an inward end and an outward end. Also, the ear irrigation device includes an input duct extending from the outward end to the inward end and terminating in a nozzle. The nozzle is adapted to direct fluid out of the body both transversely and towards the external ear when the inward end is positioned proximate to the inner portion of the external ear canal.

10 Claims, 6 Drawing Sheets

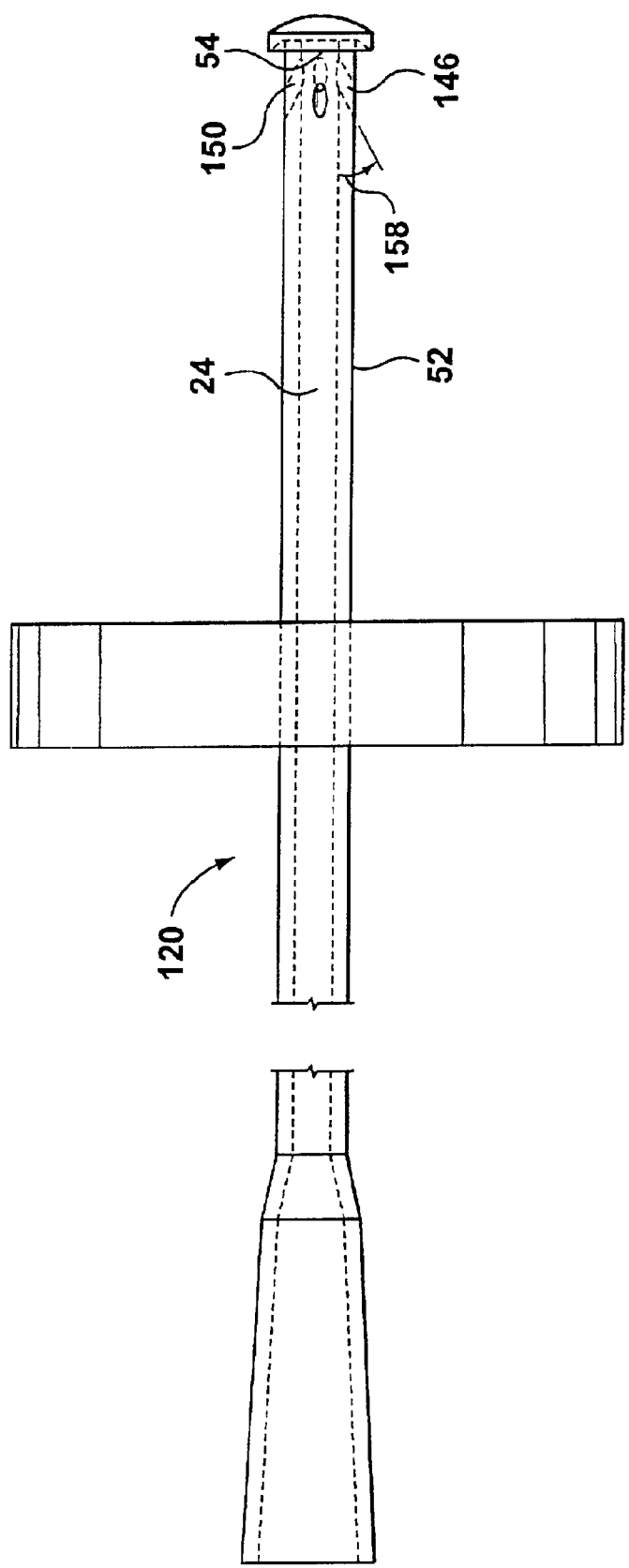

EAR IRRIGATION DEVICE

FIELD OF THE INVENTION

This invention relates to ear irrigation devices and, more particularly, an ear irrigation device for irrigation of an external ear canal with fluid.

BACKGROUND OF THE INVENTION

Irrigation devices are known which use fluid injected under pressure to remove ear wax, or cerumen, accumulated in an external ear canal. Examples of such irrigation devices are those disclosed in U.S. Pat. No. 4,206,756 (Grossan), U.S. Pat. No. 5,364,343 (Apolet et al.), and U.S. Pat. No. 6,210,358 B1 (Roger).

Each of the known devices is intended to remove cerumen which has accumulated in the external ear canal. However, each of the known devices involves the possibility of damaging the ear drum, or tympanic membrane. This is because the known irrigation devices direct the fluid inwardly, and in the general direction of the tympanic membrane.

The risk of damage to the tympanic membrane is well known, and some of the known irrigation devices include features intended to decrease this risk. For example, the irrigation device disclosed in Apolet et al. projects fluid inwardly, but generally towards wall surfaces of the external ear canal, apparently in an attempt to limit the extent to which the projected fluid strikes the tympanic membrane. However, because the device disclosed in Apolet et al. is positioned generally at an outer end of the ear canal when the fluid is projected inwardly from the device, at least some of the fluid projected from the device washes against the tympanic membrane, and the possibility of damage still exists with this device. Also, the washing of injected fluid against the tympanic membrane can cause some discomfort for some patients.

Cerumen can be pushed inwardly into the external ear canal, for example, by a patient's finger. Cerumen can also become impacted, i.e., packed into the external ear canal. Because of the risk of damage to the tympanic membrane and other structures of the ear, accumulated cerumen, and impacted cerumen deposits in the external ear canal, should only be removed by a doctor. However, with each visit to a doctor, costs are incurred. As well, the time spent by patients in attending at doctors' offices to have cerumen removed is cumulatively significant.

There continues to be a need for an ear irrigation device for preventing the accumulation of cerumen in the external ear canal which can be used by a patient without professional assistance.

SUMMARY OF THE INVENTION

In a broad aspect of the present invention, there is provided an ear irrigation device for injecting a fluid into an external ear canal extending between an external ear and a tympanic membrane. The external ear canal includes an outer portion extending inwardly from the external ear and including cerumen-producing glands and an inner portion between the tympanic membrane and the outer portion. The ear irrigation device has a longitudinally extending body including an inward end and an outward end and an input duct extending from the outward end to the inward end and terminating in a nozzle. Also, the nozzle is adapted to direct fluid out of the body transversely and towards the external ear. When the inward end of the body is positioned proximate to the inner portion of the external ear canal and fluid is directed into the input duct under pressure, the fluid exits the body through the nozzle to wash out the outer portion of the external ear canal.

In another aspect of the present invention, the nozzle of the ear irrigation device has a plurality of radially disposed output ducts formed in the inward end and in fluid communication with the input duct and an outer surface of the body and an obturator disposed at the inward end to block the input duct.

In accordance with another aspect of the invention, the nozzle includes four output ducts, and each output duct is radially spaced from the next output duct by approximately 90°.

In yet another aspect of the invention, the nozzle includes a deflector extending transversely from said inward end, and the output ducts are formed to direct fluid towards the deflector.

According to yet another aspect of the invention, the output ducts are formed to direct fluid away from the obturator.

In another aspect of the present invention, the ear irrigation device additionally includes a stop portion for positioning the inward end of the body proximate to the inner portion of the external ear canal. The stop portion extends transversely between the inward end and the outward end to abut the external ear when the inward end of the body is in the external ear canal.

According to another aspect of the present invention, there is provided a method of preventing accumulation of cerumen in an outer portion of an external ear canal extending between an external ear and a tympanic membrane. The external ear canal includes an outer portion extending inwardly from the external ear and including cerumen-producing glands and an inner portion between the tympanic membrane and the outer portion. The method includes the step of providing an ear irrigation device for irrigating the external ear canal with fluid. The ear irrigation device has a longitudinally extending body including an inward end and an outward end, and an input duct extending from the outward end through the body to the inward end and terminating in a nozzle. The nozzle is adapted to direct fluid out of the body and towards the external ear. In addition, the method includes the steps of inserting the inward end of the body of the ear irrigation device into the external ear canal until the inward end is proximate to the inner portion of the external ear canal, and supplying fluid under pressure into the input duct at the outward end. The result is that fluid exits the body through the nozzle to wash out the outer portion of the external ear canal towards the external ear.

BRIEF DESCRIPTION OF THE DRAWINGS

The invention will be better understood with reference to the drawings, in which:

FIG. 7 is a partial cross-section of another embodiment of the ear irrigation device, drawn at a larger scale.

BRIEF DESCRIPTION OF THE PREFERRED EMBODIMENT(S)

Figure 1:
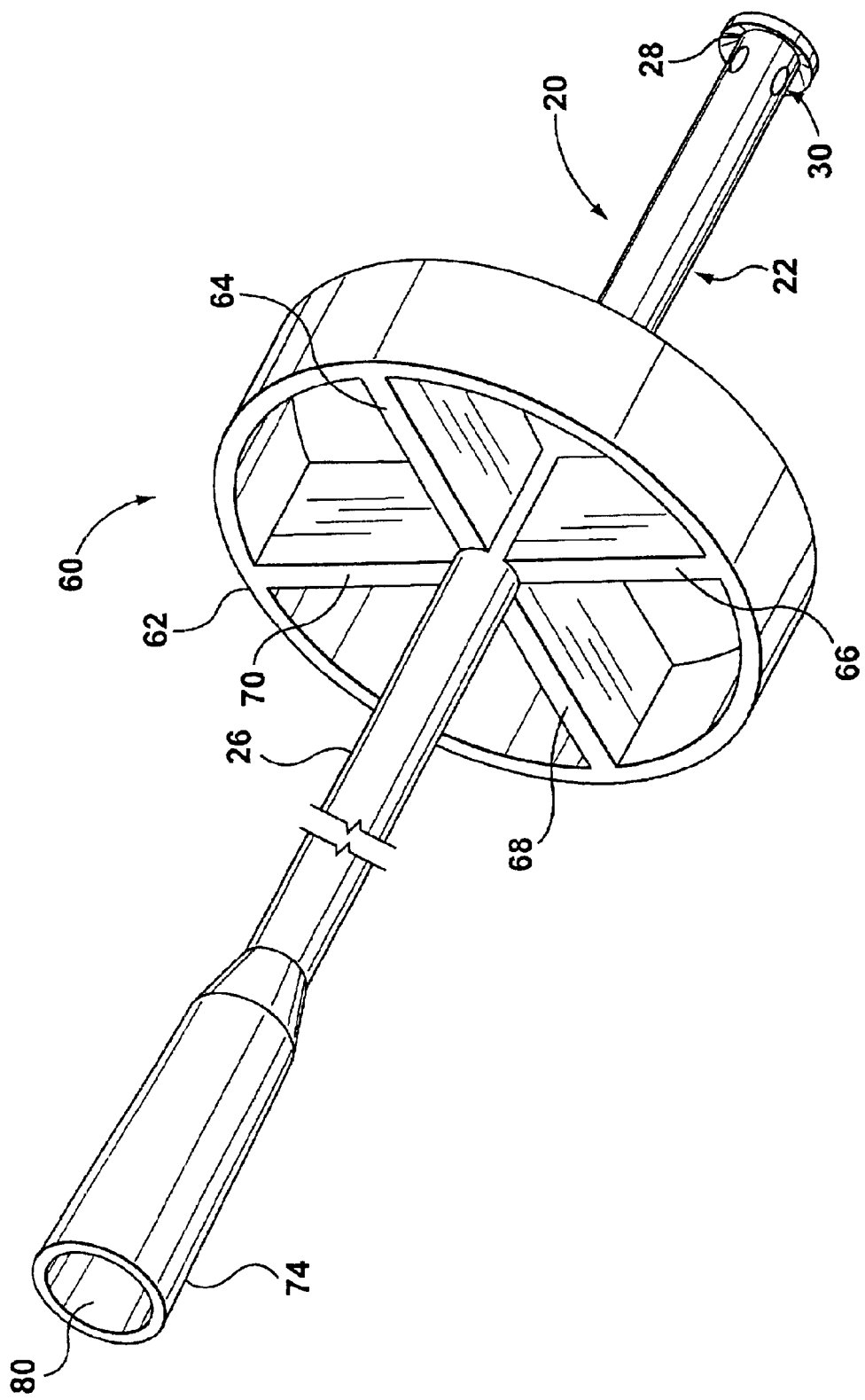
FIG. 1 is an isometric view of a preferred embodiment of the ear irrigation device.
Figure 2:
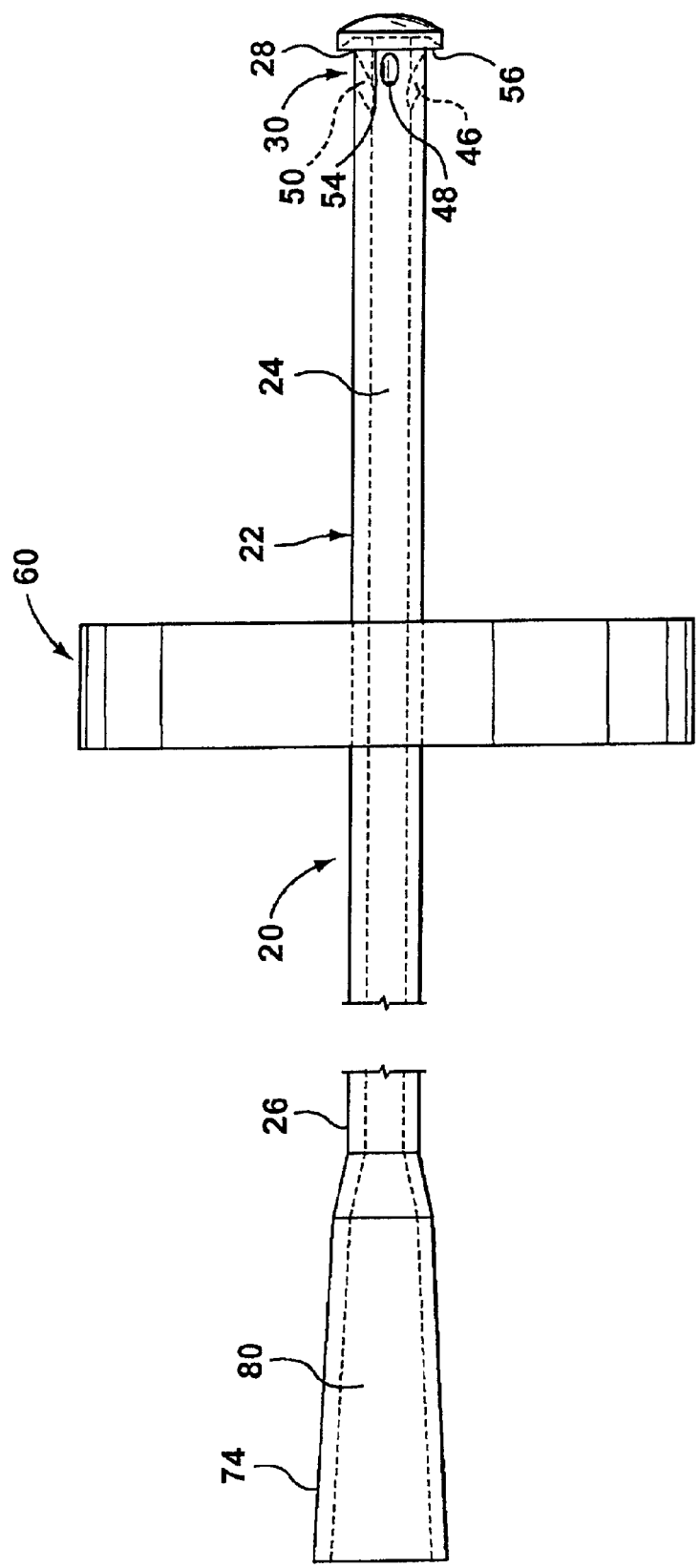
FIG. 2 is a partial cross-section of the ear irrigation device of FIG. 1.

Reference is first made to FIGS. 1 and 2 to describe a preferred embodiment of an ear irrigation device indicated generally by the numeral 20 in accordance with the invention. The ear irrigation device 20 includes a longitudinally extending body 22 having an input duct 24 extending from an outward end 26 to an inward end 28 of the body 22. As will be described in more detail, the input duct 24 terminates at the inward end 28 in a nozzle 30.

Figure 3:
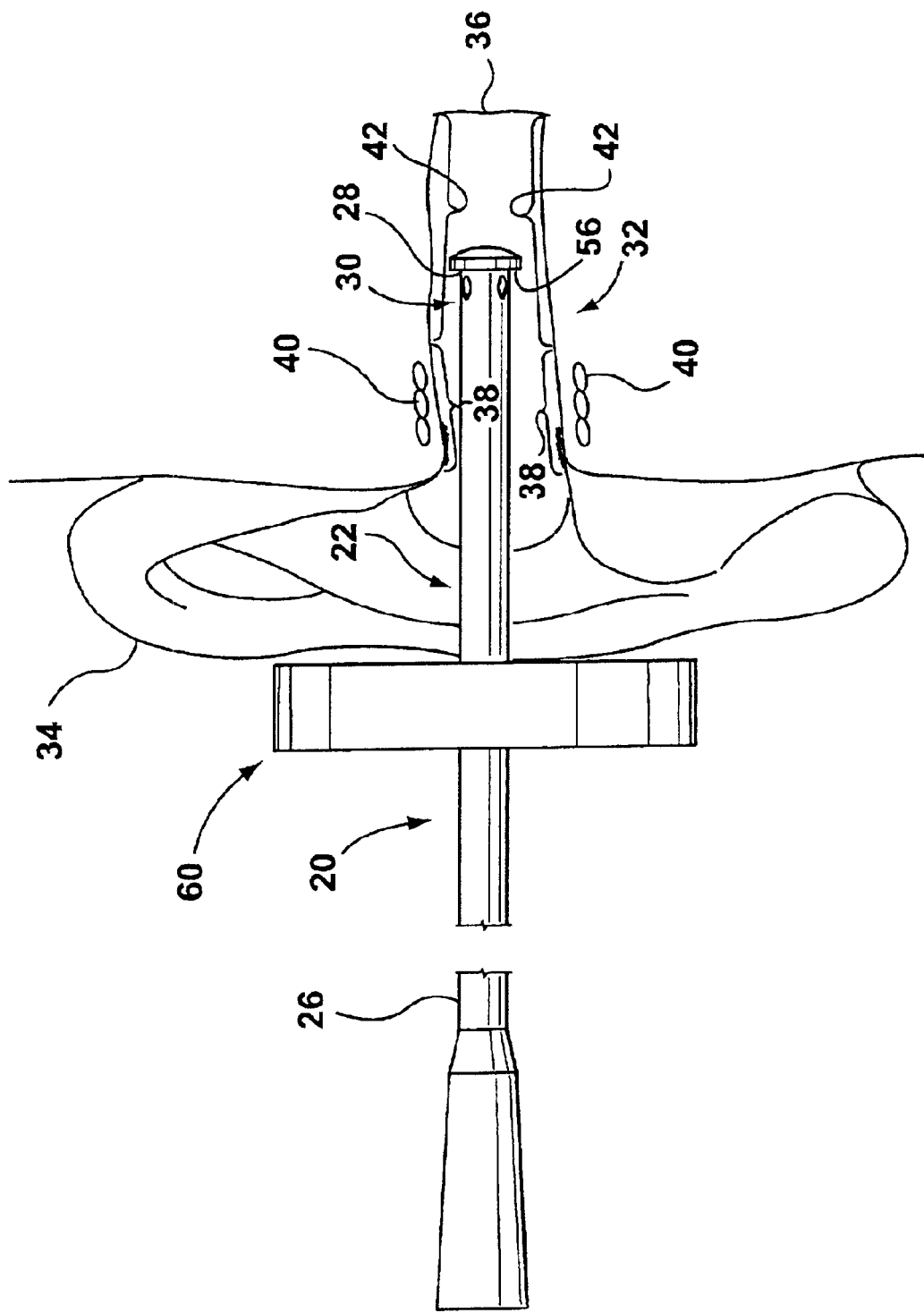
FIG. 3 is a side view of the ear irrigation device of FIG. 1 inserted in an external ear canal, drawn at a smaller scale.

As shown in FIG. 3, the inward end 28 of the body 22 is to be inserted into an external ear canal 32. The external ear canal 32 extends between an external ear 34 to a tympanic membrane 36. The external ear canal 32 includes an outer portion 38 extending inwardly from the external ear 34 and including cerumen-producing glands 40. Cerumen, or ear wax, is secreted by the cerumen-producing glands 40, so that cerumen is deposited in the outer portion 38 accordingly. The external ear canal 32, however, also includes an inner portion 42 located between the tympanic membrane 36 and the outer portion 38. The inner portion 42 does not include cerumen-producing glands.

When the inward end 28 of the body 22 is positioned proximate to the inner portion 42 of the external ear canal 32 and fluid (not shown) is directed into the input duct 24 under pressure, the fluid exits the body 22 through the nozzle 30 to wash out the outer portion 38 of the external ear canal 32 towards the external ear 34. It can be seen in FIGS. 2, 3, 4, and 7 that the nozzle 30 is adapted to direct fluid out of the body both transversely and outwardly, towards the external ear 34.

Figure 4:
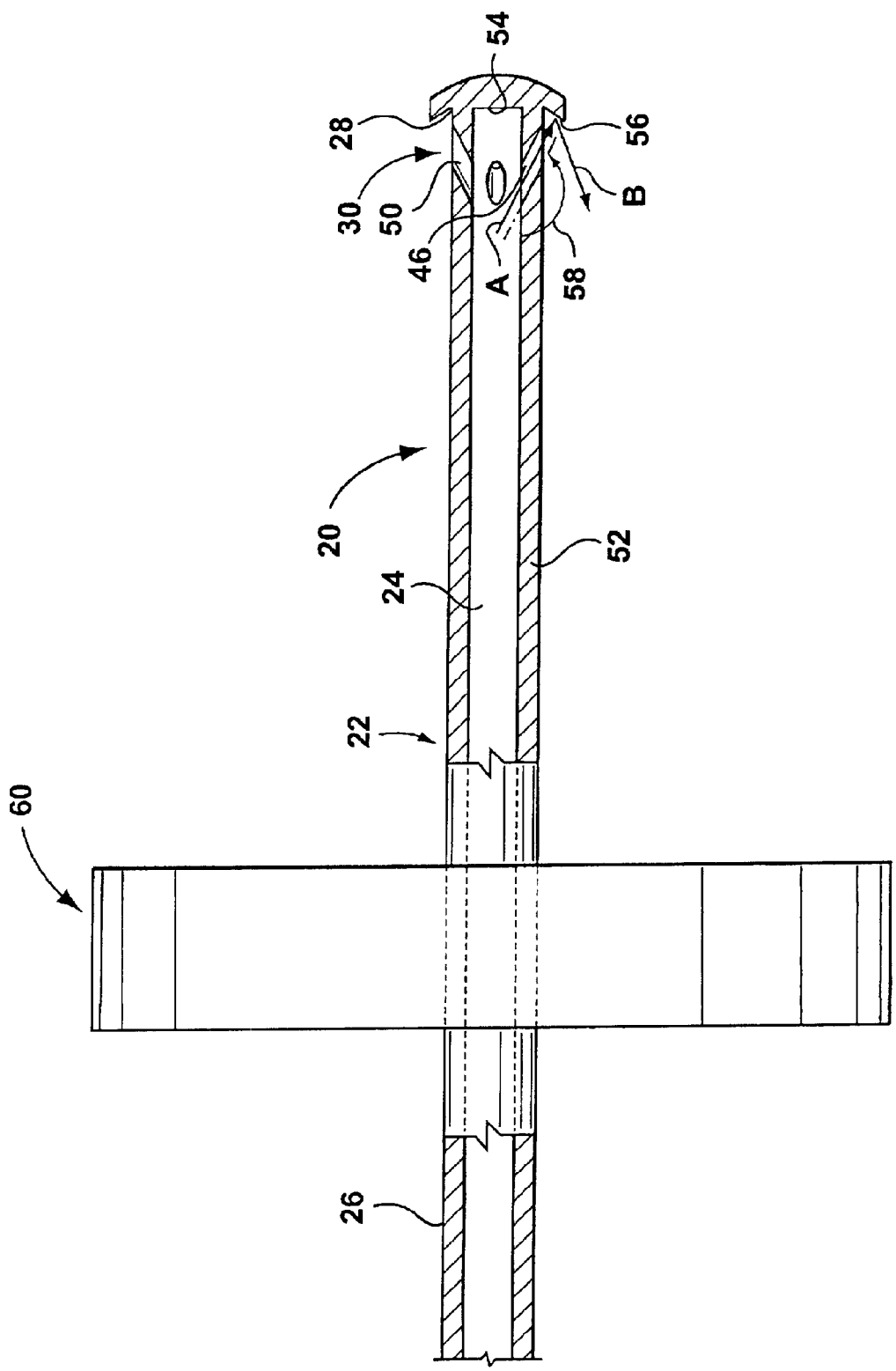
FIG. 4 is a partial cross-section of the ear irrigation device of FIG. 1, drawn at a larger scale.
Figure 5:
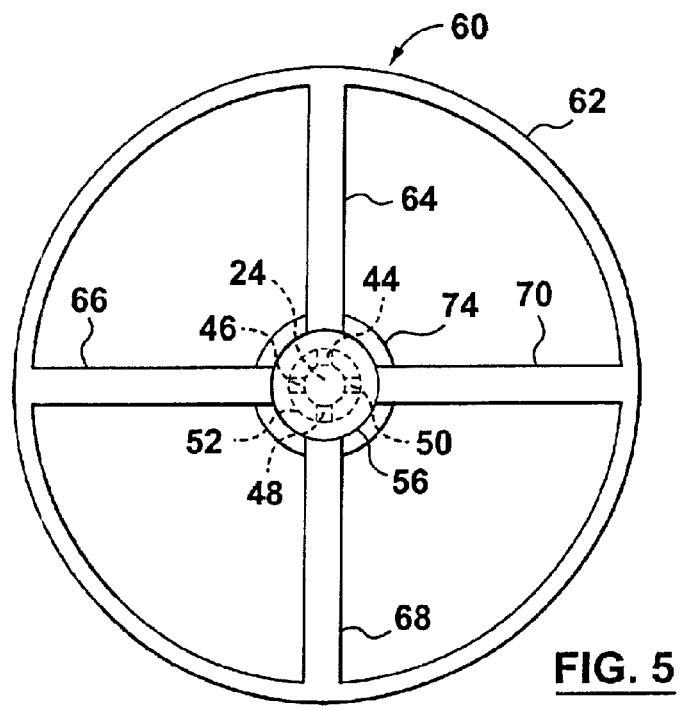
FIG. 5 is a side view of an inward end of the ear irrigation device of FIG. 1.

As can be seen in FIGS. 2, 4, and 5, it is preferred that the nozzle 30 has four radially disposed output ducts 44, 46, 48, 50. Each output duct 44, 46, 48, 50 is formed in the inward end 28 and is in fluid communication with the input duct 24 and an outer surface 52 of the body 22. Preferably, each output duct 44, 46, 48, 50 is radially spaced from the next by approximately 90°. The nozzle 30 also includes an obturator 54 disposed at the inward end 28, to block the input duct 24.

In the preferred embodiment, the nozzle 30 also includes a deflector 56 extending transversely from the inward end 28. For convenience, only output ducts 46, 50 are shown in FIGS. 2 and 4. It will be understood, however, that the four output ducts 44, 46, 48, 50, being radially disposed, are similarly formed and positioned, and the following discussion regarding output ducts 46, 50 will be understood as applying equally to all output ducts 44, 46, 48, 50.

As can be seen in FIGS. 2 and 4, in the preferred embodiment, the output ducts 46, 50 are formed to direct fluid towards the deflector 56. Arrow A in FIG. 4 represents the direction of fluid exiting the body 22 via output duct 46, to show a typical path of fluid exiting the body 22. Arrow B in FIG. 4 represents the direction taken by fluid due to deflection of the fluid by the deflector 56, after having exited the body 22 via output duct 46. Because of the angle at which fluid directed out of the output ducts 44, 46, 48, 50 strikes the deflector 56, fluid is redirected by the deflector 56 in a direction which is both transverse and outwardly, i.e., out of the external ear canal 32, towards the external ear. For simplicity, similar representations are not shown for fluid exiting output ducts 44, 48, 50. The embodiment shown in FIGS. 2 and 4 is preferred because the fluid tends to splash both transversely and outwardly from the inward end 28 when it is redirected by the deflector 56.

Each output duct 44, 46, 48, 50 forms an angle 58 with the input duct 24 which is subtended by the outer surface 52. The angle 58 is shown in FIG. 4. As will be described in more detail, it is preferred that the ear irrigation device 20 is provided in a version sized for use by an adult, and also in a version sized for use by a child. Preferably, in the version of the ear irrigation device 20 made for use by an adult the angle 58 is approximately 150°. It is also preferred that the angle 58 is approximately 160° in the version of the ear irrigation device 20 designed for use by children within a certain range of ages, as will be described.

It can be seen from the foregoing that positioning the inward end 28 proximate to the inner portion 42 of the external ear canal 32 is important. As shown in FIG. 3, the preferred embodiment of the ear irrigation device 20 also includes a stop portion 60 which, as can be seen in FIG. 3, positions the inward end 28 of the body 22 proximate to the inner portion 42 of the external ear canal 32. In particular, the stop portion 60 prevents insertion of the inward end 28 of the body 22 too far into the external ear canal 32. As will be described, because the dimensions of a typical adult's external ear canal differ substantially from those of a child, the ear irrigation device 20 is preferably dimensioned appropriately for use by a typical adult or by a child, as the case may be.

Although various arrangements could be employed, it is preferred that the stop portion 60 includes a rim 62 for abutting the external ear 34 when the inward end 28 of the body 22 is positioned proximate to the inner portion 42 of the external ear canal 32, as shown in FIGS. 1 and 5. The stop portion 60 preferably also includes four spokes 64, 66, 68, 70 extending transversely from the body 22 to the rim 62 to space the rim 62 apart from the body 22. Each spoke 64, 66, 68, 70 is preferably radially spaced from the next by approximately 90°. This arrangement is preferred because it permits fluid to exit the external ear canal 32 at the external ear 34 relatively unimpeded by the stop portion 60.

Figure 6:
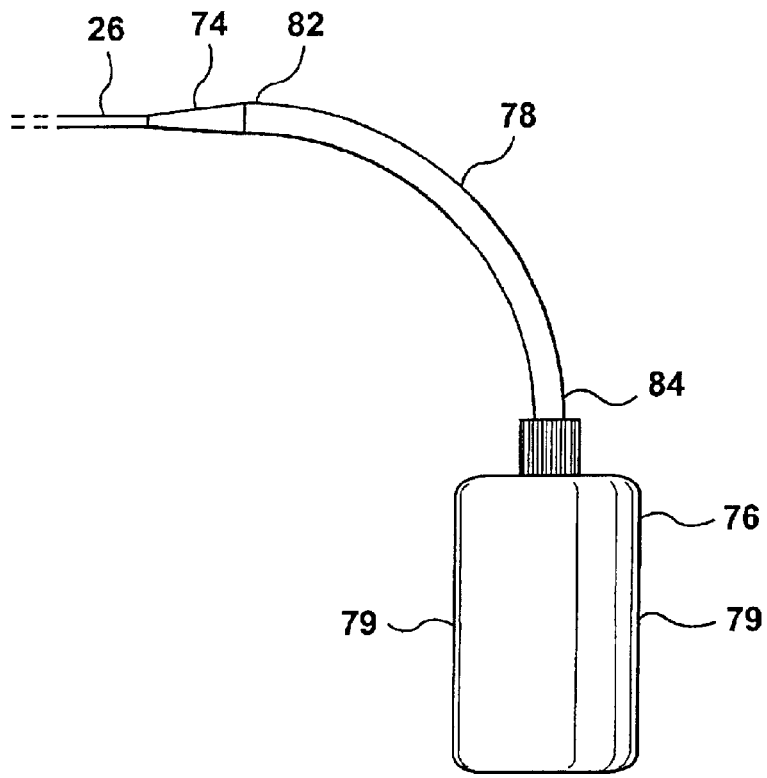
FIG. 6 is a side view of a fluid reservoir attached to an input extension portion of the ear irrigation device, drawn at a smaller scale.

Various means can be employed to inject fluid under pressure into the output duct 24 at the outward end 26. It is preferred that the ear irrigation device 20 also includes an input extension portion 74 extending from the outward end 26 of the body 22 for use with a fluid reservoir 76 and a reservoir tube 78, as shown in FIG. 6. As is known in the art, the input extension portion 74, which includes an input extension duct 80, is adapted to receive an end 82 of the reservoir tube 78. The input extension duct 80 is in fluid communication with the input duct 24 at the outward end 26. The reservoir tube 78 also has an end 84 attached to the fluid reservoir 76, so that the fluid reservoir 76 is in fluid communication with the input extension duct 80, through the reservoir tube 78. As is known in the art, the fluid reservoir 76 preferably is a flexible plastic bottle adapted to expel fluid therein under pressure through the tube 78. For example, where the fluid reservoir 76 is a plastic bottle with flexible sides 79, then in response to squeezing the fluid reservoir 76, fluid is injected through the reservoir tube 78, into the input extension duct 80, and ultimately into the input duct 24 under pressure. Preferably, the fluid reservoir 76 is of the type of bottle or syringe known in the art which can easily be operated by a user (not shown) with one hand.

It will be clear to those skilled in the art that the ear irrigation device 20 is not designed for removal of impacted cerumen, or significant accumulations of cerumen. The ear irrigation device 20 is only for use after substantially all cerumen has been removed from the external ear canal 32 by a doctor. Once the external ear canal 32 has been cleared of substantially all cerumen, the ear irrigation device 20 can be used.

The advantages and benefits of the ear irrigation device 20 can now been seen. Provided that any impacted cerumen has been recently removed by a doctor, the user can use the ear irrigation device 20 safely, without requiring the assistance of a doctor or other medical professional. The ear irrigation device 20 can be used on a regular daily or weekly basis to prevent the accumulation of cerumen, thereby minimizing the user's visits to the doctor. The ear irrigation device 20 enables the user to spray the fluid outwardly from a particular position in the external ear canal 32, namely, a position proximate to the inner portion 42, so that the fluid washes outwardly over the outer portion 38, where cerumen is secreted and initially deposited, to the external ear 34 and out. The ear irrigation device 20 is configured to take advantage of a particular physical feature, namely, the lack of cerumen-producing glands in the inner portion 42. If used in the manner described, the ear irrigation device 20 does not direct fluid into the external ear canal 32 towards the tympanic membrane 36, directly or indirectly.

In the preferred embodiment, the ear irrigation device 20 is constructed of lightweight and soft, flexible plastic material, as is known in the art. The material used should be soft, so as to minimize the possibility of trauma to the external ear canal 32.

Any suitable fluid known in the art can be used with the ear irrigation device 20. For example, the fluid can be warm water, or a solution of 50% hydrogen peroxide and 50% water, as is known in the art. Preferably, the fluid is a solution including hydrogen peroxide so that the cerumen is dissolved at least in part, as well as washed out of the external ear canal 32. The solution can also include camphor to provide a cooling effect for the comfort of the user, as is known in the art. However, those skilled in the art will be aware of a variety of fluids which would be suitable for use in the ear irrigation device 20.

In a typical adult, the outer portion 38 is a cartilaginous section approximately 8 mm. in length, and the outer portion 38 is a bony section. The external ear canal 32 has an overall length of approximately 2.5 cm. in a typical adult.

Preferably, in the version of the ear irrigation device 20 for use by an adult, the body 22 is generally right cylindrical in shape and approximately 2 mm. in diameter, with the input duct 24 being approximately 1 mm. in diameter. It is preferred as well that the stop portion 60 is positioned approximately 17 mm. from the inward end 28. Also, in the ear irrigation device 20 configured for use by an adult, the deflector 56 is preferably approximately 3 mm. in diameter. The rim 62, as shown in FIG. 5, preferably describes a circle when viewed from the inward end 28 of the body 22. Preferably, the rim 62 is approximately 18 mm. in diameter, for ease of use by an adult. As noted above, it is preferred that the angle 58 is approximately 150°.

The different dimensions of a child's external ear canal and related structures require a smaller version of the ear irrigation device 20. The ear irrigation device 20 sized for use by a typical child between 7 and 15 years old includes a body 22 which is approximately 1.3 mm. in diameter, with the input duct 24 being approximately 0.70 mm. in diameter. In the version of the ear irrigation device 20 configured for use by a child, the stop portion 60 is positioned approximately 12 mm. from the inward end 28, and the deflector 56 is preferably approximately 2 mm. in diameter. The rim 62 in the child's version of the ear irrigation device 20 is preferably approximately 12 mm. in diameter. As noted above, it is preferred that the angle 58 is approximately 160° in the child's version of the ear irrigation device 20.

In use, the inward end 28 of the body 22 is inserted into the external ear canal 32 until the inward end 28 is proximate to the inner portion 42. The positioning of the inward end 28 in the external ear canal 32 is shown in FIG. 3. The user supplies fluid under pressure to the input duct 24 at the outward end 26. The fluid could be provided when the user squeezes the fluid reservoir 76, as discussed. The fluid exits the body 22 via the nozzle 30, and the nozzle 30 directs the fluid out of the body 22 both transversely and towards the external ear 34. Accordingly, the fluid washes out the outer portion 38 and towards the external ear 34, to exit the external ear canal 32.

In the preferred embodiment, the fluid exits the body 22 via the four output ducts 44, 46, 48, 50 towards the deflector 56. The fluid is redirected by the deflector 56 so that the fluid is directed both transversely and outwardly, towards the external ear 34. The gaps between the spokes 64, 66, 68, 70 in the stop portion 60 permit the fluid to exit the external ear canal 32.

An alternative embodiment 120 of the ear irrigation device is shown in FIG. 7. In the ear irrigation device 120, preferably four output ducts are formed in the inward end 28. For convenience, only output ducts 146 and 150 are shown in FIG. 7. It is also preferred that each output duct is radially spaced from the next by approximately 90°. However, in this alternative embodiment, the output ducts 146, 150 are formed to direct fluid away from the obturator 54. An angle 158 is defined in this alternative embodiment by each output duct and the input duct 24 and subtended by the outer surface 52. Preferably, the angle 158 is approximately 30° in the versions of the ear irrigation device 120 made for use by children and by adults.

It will be evident to those skilled in the art that the invention can take many forms, and that such forms are within the scope of the invention as claimed. For example, a larger or a smaller number of output ducts could be used, or other forms of nozzles could be used to achieve a flow of fluid exiting the body which is directed transversely and outwardly. Therefore, the spirit and scope of the appended claims should not be limited to the description of the preferred versions contained herein.

I claim:

1. An ear irrigation device for injecting a fluid into an external ear canal extending between an external ear and a tympanic membrane, the external ear canal including an outer portion extending inwardly from the external ear and including cerumen-producing glands and an inner portion disposed between the tympanic membrane and the outer portion, the ear irrigation device having:

a longitudinally extending body including an inward end and an outward end, the inward end being positionable in the inner portion of the external ear canal with the outward end extending beyond the external ear;

an input duct extending from the outward end to the inward end and terminating in a nozzle at the inward end;

the nozzle being positioned substantially at the inward end and having a plurality of output ducts, each said output duct extending from said input duct to an outer surface of the body, and an obturator blocking the input duct at the inward end;

the output ducts being substantially equally radially spaced apart from each other respectively;

the nozzle including a deflector extending transversely from said body with a deflector surface at least partially spaced apart from the outer surface of the body; and said output ducts being formed to direct fluid out of the body towards the deflector surface, the deflector surface being positioned to redirect the fluid substantially towards the outward end of the body.

2. An ear irrigation device according to claim 1 additionally including a stop portion for positioning the nozzle in the inner portion of the external ear canal and proximate to the tympanic membrane, the stop portion extending transversely between the inward end and the outward end of the body to abut the external ear when the inward end of the body is in the inner portion of the external ear canal, the stop portion including a rim for engaging the external ear when the inward end of the body is located in the inner portion of the external ear canal and at least one spoke extending transversely from the body to the rim to position the rim and to permit the fluid to drain through the stop portion.

3. An ear irrigation device according to claim 2 additionally including an input extension portion extending from the outward end of the body, the input extension portion including an input extension duct in fluid communication with the input duct in the body at the outward end, and an adaptor for receiving and sealably coupling with a container output adaptor such that the fluid is dispensable from a fluid container through the input extension portion and into the input duct under pressure.

4. An ear irrigation device for injecting a fluid into an external ear canal extending between an external ear and a tympanic membrane, the external ear canal including an outer portion extending inwardly from the external ear and including cerumen-producing glands and an inner portion between the outer portion and the tympanic membrane, the ear irrigation device having:

a longitudinally extending body including an inward end and an outward end, the inward end being positionable in the inner portion of the external ear canal with the outward end extending beyond the external ear;

an input duct extending from the outward end to the inward end;

four output ducts formed in said inward end of the body and extending from said input duct to an outer surface of the body, each output duct being radially spaced from the next output duct by approximately 90°;

an obturator disposed at said inward end to block the input duct; and said output ducts being formed to direct fluid away from the obturator and substantially towards the outward end of the body.

5. A method of preventing accumulation of cerumen in an outer portion of an external ear canal, the method comprising the steps of:

(a) providing an ear irrigation device for irrigating an external ear canal with a fluid, the external ear canal extending between an external ear and a tympanic membrane, the external ear canal including an outer portion extending inwardly from the external ear and including cerumen-producing glands and an inner portion disposed between the tympanic membrane and the outer portion, the ear irrigation device having:

a longitudinally extending body including an inward end and an outward end, the inward end being positionable in the inner portion of the external ear canal with the outward end extending beyond the external ear;

an input duct extending from the outward end through the body to the inward end and terminating in a nozzle at the inward end;

the nozzle being adapted to direct fluid out of the body and towards the outer portion and the external ear when the nozzle is positioned in the inner portion;

the nozzle including a deflector extending transversely from said body with a deflector surface at least partially spaced apart from the outer surface of the body; and said output ducts being formed to direct fluid out of the body towards the deflector surface, the deflector surface being positioned to redirect the fluid substantially towards the outer portion and the external ear;

(b) inserting the inward end of the body into the external ear canal until the inward end is in the inner portion of the external ear canal; and (c) supplying the fluid under pressure into the input duct at the outward end such that the fluid is directed by the nozzle towards the outer portion and the external ear, to wash cerumen out of the outer portion.

6. An ear irrigation device for injecting a fluid into an external ear canal extending between an external ear and a tympanic membrane, the external ear canal including an outer portion extending inwardly from the external ear and including cerumen-producing glands and an inner portion disposed between the outer portion and the tympanic membrane, the ear irrigation device having:

a longitudinally extending body including an inward end and an outward end, the inward end being positionable in the inner portion with the outward end extending beyond the external ear, the body having an outer surface;

an input duct extending from the outward end through the body to the input end, the input duct being substantially coaxial with the body;

a deflector positioned transversely to the input duct and including a deflector surface at least partially spaced apart from the outer surface of the body;

at least one output duct extending from the input duct to the external surface, said at least one output duct and said input duct defining an angle therebetween which is between approximately 150° and approximately 160°;

said at least one output duct being formed to direct fluid towards the deflector surface; and the deflector being formed for redirecting fluid substantially towards the outward end of the body.

7. An ear irrigation device according to claim 6 additionally including a stop portion for positioning the nozzle in the inner portion of the external ear canal and proximate to the tympanic membrane, the stop portion extending transversely between the inward end and the outward end of the body to abut the external ear when the inward end of the body is in the inner portion of the external ear canal, the stop portion including a rim for engaging the external ear when the inward end of the body is located in the inner portion of the external ear canal and at least one spoke extending transversely from the body to the rim to position the rim and to permit the fluid to drain through the stop portion.

8. An ear irrigation device for injecting a fluid into an external ear canal extending between an external ear and a tympanic membrane, the external ear canal including an outer portion extending inwardly from the external ear and including cerumen-producing glands and an inner portion disposed between the outer portion and the tympanic membrane, the ear irrigation device having:

a longitudinally extending body including an inward end and an outward end, the inward end being positionable in the inner portion with the outward end extending beyond the external ear, the body having an outer surface;

an input duct extending from the outward end through the body to the input end, the input duct being substantially coaxial with the body;

at least one output duct extending from the input duct to the external surface, said at least one output duct and said input duct defining an angle therebetween which is approximately 30°; and an obturator positioned transversely to the input duct at the inward end, said at least one output duct being formed for directing fluid away from the obturator and substantially towards the outward end of the body.

9. An ear irrigation device according to claim 8 additionally including a stop portion for positioning the nozzle in the inner portion of the external ear canal and proximate to the tympanic membrane, the stop portion extending transversely between the inward end and the outward end of the body to abut the external ear when the inward end of the body is in the inner portion of the external ear canal, the stop portion including a rim for engaging the external ear when the inward end of the body is located in the inner portion of the external ear canal and at least one spoke extending transversely from the body to the rim to position the rim and to permit the fluid to drain through the stop portion.

10. An ear irrigation device for injecting a fluid into an external ear canal extending between an external ear and a tympanic membrane, the external ear canal including an outer portion extending inwardly from the external ear and including cerumen-producing glands and an inner portion disposed between the tympanic membrane and the outer portion, the ear irrigation device having:

an elongate body with an inward end and an outward end, the inward end being positionable in the inner portion of the external ear canal, the outward end extending beyond the external ear when the inward end is in the inner portion;

the body having an outer surface;

an input duct extending from the outward end to the inward end;

a deflector extending from the body and including a deflector surface at least partially spaced apart from the outer surface of the body;

at least one output duct formed in the inward end of the body, said at least one output duct extending from the input duct to the outer surface between the outward end and the deflector, and positioned to direct fluid from the input duct towards the deflector surface; and the deflector surface being positioned to redirect the fluid towards the outward end of the body.

* * * * *